(12) United States Patent
Den Hartog et al.

(10) Patent No.: US 10,716,524 B2
(45) Date of Patent: Jul. 21, 2020

(54) AUTOMATIC EMBOLIZATION AGENT VISUALISATION IN X-RAY INTERVENTIONS

(71) Applicant: KONINKLIJKE PHILIPS N.V., Eindhoven (NL)

(72) Inventors: Markus Johannes Harmen Den Hartog, Eindhoven (NL); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 161 days.

(21) Appl. No.: 15/535,495

(22) PCT Filed: Dec. 14, 2015

(86) PCT No.: PCT/EP2015/079514
§ 371 (c)(1),
(2) Date: Jun. 13, 2017

(87) PCT Pub. No.: WO2016/096676
PCT Pub. Date: Jun. 23, 2016

(65) Prior Publication Data
US 2017/0340301 A1      Nov. 30, 2017

(30) Foreign Application Priority Data
Dec. 18, 2014  (EP) ................................. 14307072

(51) Int. Cl.
*A61B 6/00*   (2006.01)
*G06T 5/50*   (2006.01)
*G06T 7/00*   (2017.01)

(52) U.S. Cl.
CPC .............. *A61B 6/481* (2013.01); *A61B 6/487* (2013.01); *A61B 6/504* (2013.01); *A61B 6/5217* (2013.01);
(Continued)

(58) Field of Classification Search
CPC ......... A61B 6/469; A61B 6/481; A61B 6/487; A61B 6/504; A61B 6/5217; G06T 5/50;
(Continued)

(56) References Cited

U.S. PATENT DOCUMENTS

| | | | |
|---|---|---|---|
| 2007/0208277 A1 | 9/2007 | Rioux | |
| 2008/0051648 A1* | 2/2008 | Suri | ...................... A61B 6/481 600/407 |

(Continued)

FOREIGN PATENT DOCUMENTS

| | | |
|---|---|---|
| WO | 20110151752 A1 | 12/2011 |
| WO | 2014009827 A2 | 1/2014 |

OTHER PUBLICATIONS

Hubbell, J.H. et al "Tables of X-Ray Mass Attenuation Coefficients and Mass Energy-Absorption Coefficients", National Institute of Standards and Technology 2014.
(Continued)

*Primary Examiner* — Amanda K Hulbert

(57) ABSTRACT

Image processing methods and related systems (IPS) to process imagery (F) acquired during deposition of a substance at a region of interest, ROI The methods and systems allow visualizing in a graphics display (GD) various aspects of the deposited substance and/or determining, based on the imagery, the amount of said substance deposited at the ROI.

13 Claims, 4 Drawing Sheets

(52) U.S. Cl.
CPC .............. *G06T 5/50* (2013.01); *G06T 7/0016* (2013.01); *A61B 6/469* (2013.01); *G06T 2207/10121* (2013.01); *G06T 2207/20216* (2013.01); *G06T 2207/20224* (2013.01); *G06T 2207/30104* (2013.01)

(58) Field of Classification Search
CPC ......... G06T 7/0016; G06T 2207/10121; G06T 2207/20216; G06T 2207/20224; G06T 2207/30104
USPC ........................................................ 600/431
See application file for complete search history.

(56) References Cited

U.S. PATENT DOCUMENTS

| | | |
|---|---|---|
| 2008/0275467 A1 | 11/2008 | Liao |
| 2009/0116711 A1* | 5/2009 | Larson .................. G06T 7/0016 382/128 |
| 2010/0329526 A1 | 12/2010 | Pfister et al. |
| 2011/0200165 A1* | 8/2011 | Pietsch .............. A61K 41/0019 378/14 |
| 2012/0099768 A1 | 4/2012 | Helm |
| 2013/0190615 A1* | 7/2013 | Royalty .................. A61B 6/481 600/431 |
| 2013/0345559 A1 | 12/2013 | Haemmerich |
| 2014/0037049 A1 | 2/2014 | Langan |
| 2014/0270437 A1 | 9/2014 | Shreiber |

OTHER PUBLICATIONS

Copeland, A.D. et al "Spatio-Temporal Data Fusion for 3D+T Image Reconstruction in Cerebral Angiography", Medical Imaging, IEEE Transactions, vol. 29, Issue 6, 2010.

Ross, James C. et al "Motion Correction for Augmented Fluoroscopy—Application to Liver Embolization", IEEE, 2008.

* cited by examiner

AUTOMATIC EMBOLIZATION AGENT VISUALISATION IN X-RAY INTERVENTIONS

CROSS-REFERENCE TO PRIOR APPLICATIONS

This application is the U.S. National Phase application under 35 U.S.C. § 371 of International Application No. PCT/EP2015/079514, filed on Dec. 14, 2015, which claims the benefit of European Patent Application No. 14307072.0, filed on Dec. 18, 2014. These applications are hereby incorporated by reference herein.

FIELD OF THE INVENTION

The invention relates to image processing methods, to image processing systems, to a computer program element and to a computer readable medium.

BACKGROUND OF THE INVENTION

In some interventional X-Ray procedures it is common to inject an embolization agent into the patient to effect various treatments for instance, AVMs (Arteriovenous Malformations) or tumors. For example, in order to stem growth of cancerous tissue or of an AVM (arteriovenous malformation) its arterial feeders may be intentionally embolized to shut down the blood supply (AVM) and/or stop nutrient supply to the cancer or growth (such as in transcatheter arterial chemoembolization (TACE)). This type of intervention, called medical embolization, may be brought about by administering an embolization agent at a desired location (region of interest (ROI)) in the human body by way of a catheter tube. The embolization agent is essentially a liquid volume or mass of glue comprising small beads suspended in a carrier liquid through which the occlusion at the diseased location effected. During such embolization interventions it is pre-eminent to ensure that it is only the targeted arterial feeders that are blocked off but sound vessels are not. At present the position of emboli is monitored by acquiring one or more fluoroscopic projection images. Because of radiation opacity of the embolus and/or of the carrier fluid, projective "footprints" are discernible in said fluoroscopic images thereby providing clues to an interventionist radiological about the embolus' whereabouts.

The embolization agents are usually poorly visible under X-ray fluoroscopy. To help better visualize the deposition of embolization agent, subtraction techniques are regularly used which eliminate the background and leave only the deposited embolization agent. However, using existing subtraction techniques in this context have proved in the past remarkably cumbersome and fiddly. In particular, they have relied on selection of mask images, requiring a frame ("mask") selection every few fluoroscopy runs. The resulting subtraction image shows generally only a tiny black smear of deposited embolization agent, which is very hard to distinguish from subtraction artefacts and background noise.

Another issue with embolization procedures is that in most trans-arterial embolization (TAE) procedures it is important to estimate the amount of deposited material in the target tissue. The estimate might be used to predict the clinical outcome or it might be used to check if part of the injected material was deposited elsewhere. However, to achieve these estimates, the use of expensive additional equipment is usually necessary.

SUMMARY OF THE INVENTION

The may be a need in the art for alternative methods and/or related system to aid monitoring deposition of substances that address at least some of the deficiencies noted above.

The object of the present invention is solved by the subject matter of the independent claims where further embodiments are incorporated in the dependent claims. It should be noted that the following described aspect of the invention equally applies to the image processing methods, to the computer program element and to the computer readable medium.

According to a first aspect of the invention there is provided an image processing system, comprising:

an input port configured to receive a plurality of images acquired of a region of interest, ROI, in a specimen at different instants before, during or after deposition of substance at or around said ROI;

an image combiner configured to combine i) a first image from a combination of one or more of the plurality of said images acquired up to a first instant and ii) a second image from a combination of one or more of the plurality of said images acquired up to a second instant;

a subtractor configured to subtract the first image from the second image, to obtain a difference image that represents a volume of said substance accumulated between the first and second instant, wherein at least one of the second image and the first image is combined from more than one of the images;

an output port configured to output said difference image.

With the proposed system, it is no longer necessary to use a specific mask image. The proposed system can use any of the acquired images, not necessarily only a specific mask image. The system frees the user from the constraint of only being able to visualize the depositions that occurred between the latest mask image and the current image. The proposed system allows the user to arbitrarily compose or define time intervals and to then examine or visualize the deposition in the defined time intervals in detail based on a selection from all previously acquired images. The system allows visualizing the deposition of the substance as a function of time during parts of intervention or during the complete intervention.

According to one embodiment, the first image or the second image is an average or a spatially and/or temporally filtered image formed from images acquired up to the first or second instant, respectively.

According to one embodiment, the system operates to output a plurality of difference images for different first and/or second instants, the system further comprising a visualizer configured to effect accumulative or sequential display of said plurality of difference images on a display unit. In the sequential display, the plurality of difference images are displayed one after the other, with the next difference image being displayed instead of the earlier one. In the accumulative display, a next difference image is not displayed instead of the earlier difference image being displayed, but is superimposed thereon. That is, the difference images are accumulatively superimposed onto each other, one after the other. This allows visualizing changes in shape and motion of the deposited substance.

According to one embodiment, the at least two of said difference images are displayed in different visual renderings.

According to one embodiment, the system includes a ROI focused motion compensator that operates to register, before the image subtraction, the plurality of images to motion compensate for motion of the ROI between acquisition of individual images.

According to one embodiment, the motion compensator cooperates with a landmark identifier configured to identify across the images a landmark that corresponds to the ROI or to a device operative to deposit said fluid.

According to one embodiment, the first and/or second instant is/are user adjustable.

According to one embodiment, the number of the images combined by the image combiner into the first image or the second image is user adjustable to thereby adjust a time resolution at which the accumulation of the fluid is displayed.

According to one embodiment, the system comprises a contrast measuring unit that measures a quantity of the accumulated substance based on the difference image and based on a given X-ray absorption characteristic of the X-ray absorbent fluid.

According to one embodiment, the system further comprises a substance deposition monitor configured to compare the volume of said substance administered to the specimen between the two instants with the measured quantity said volume of substance deposited as per the difference image, the deposition monitor configured to issue an alert signal if a discrepancy between the two volumes exceeds a threshold.

In other words, in one embodiment, the system affords an in-image based determination of the amount of substance deposited at the ROI. This is useful for trans-arterial embolization (TAE) procedures to estimate the amount of deposited material in the target tissue. The estimate might be used to predict the clinical outcome or it might be used to check if part of the injected material was deposited elsewhere.

In sum, what is proposed herein in one embodiment is to estimate the quantity of the deposited embolization agent in a specific region of area, using 2D X-ray imaging and advanced subtraction techniques. The proposed system can be used to estimate the flow rate of the agent leaving the catheter or flowing through a specific (branching) vessel. The result of the measurements could be visualized and/or converted into audio cues, one or both in real-time if required, to aid the user during the procedures or could be used in reporting/clinical studies.

One advantage of the proposed system is that the user is provided with quantitative injection information, without the need of using different techniques/modalities like measuring catheters or (Cone Beam) CT that might slow down the procedure significantly and/or may not be possible to achieve in real-time.

The image-based contrast measurement is also in accord with a second aspect of the invention which is an image processing system, comprising:

an input port configured to receive a plurality of projection images acquired of a region of interest, ROI, in a specimen at different instants before, during or after deposition of a substance at or around said ROI;

a subtractor configured to subtract a second image from a first image (MI), each based on one or more of the images, to obtain a difference image that represents a volume of said substance accumulated between a first and a second instant;

a contrast measuring unit that measures a quantity of the accumulated substance based on the difference image and based on a given X-ray absorption characteristic of the X-ray absorbent substance; and an output port configured to output a numerical indication of the measured quantity.

Although the system is explained with reference to embolization agents, the system may be put to good use for monitoring deposition of any substance having a relatively high viscosity and sufficient radio opacity and that exhibits relatively slow motion and relatively long residence time after deposition. In particular, the substance (such as embolic material) is different from contrast agent ("dye") usually used in angiography, the substance envisaged herein having a higher viscosity than contrast agent and those substances move or change shape slower than contrast agent does, as the contrast agent is essentially suspended in blood and the motion of a contrast agent bolus is determined by the blood flow (unlike the substances envisaged herein).

BRIEF DESCRIPTION OF THE DRAWINGS

Exemplary embodiments of the invention will now be described with reference to the following drawings wherein.

DETAILED DESCRIPTION OF EMBODIMENTS

Figure 1:
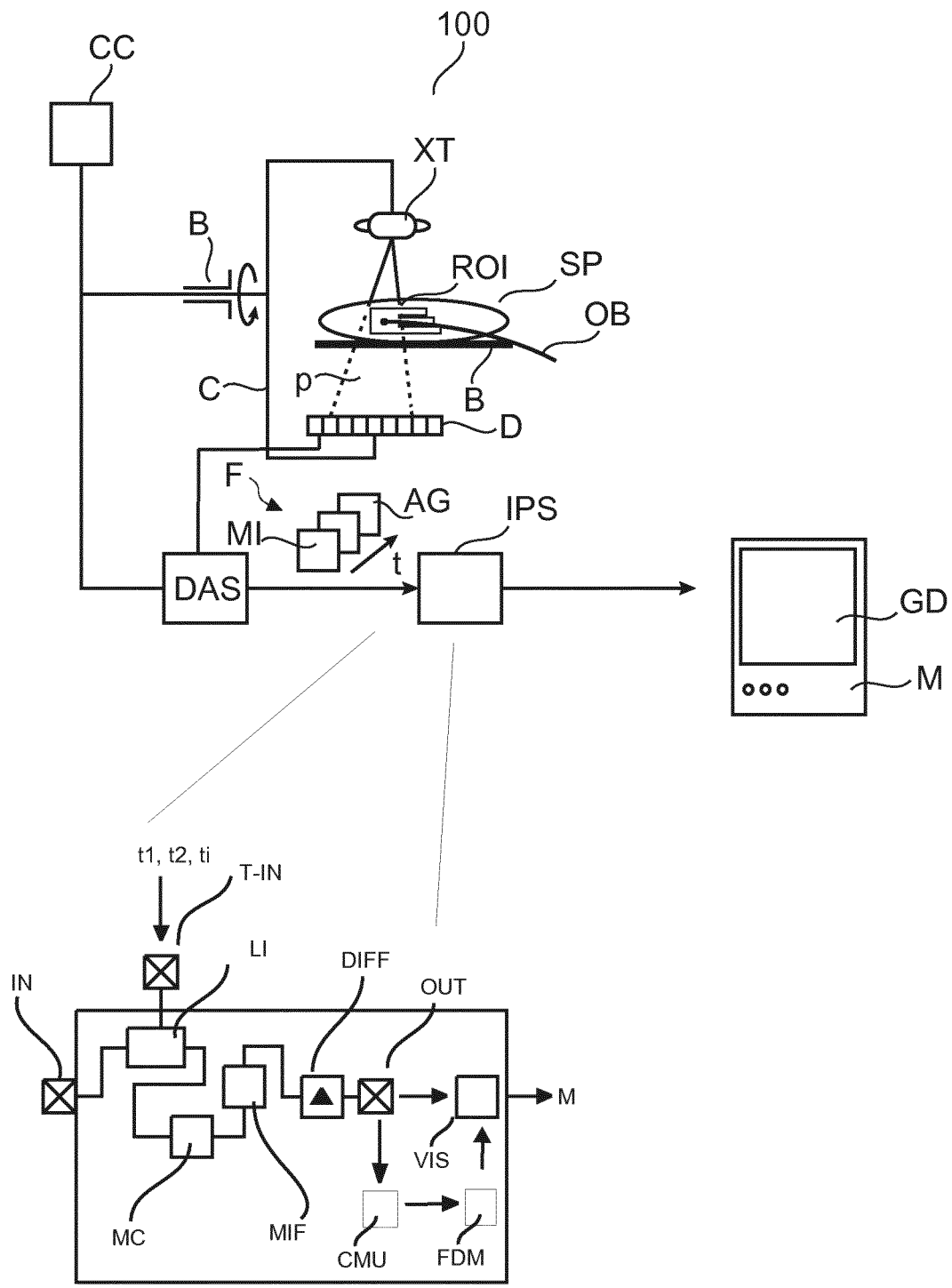
FIG. 1 shows an imaging arrangement to support an intervention.

With reference to FIG. 1, the basic components of a fluoroscopic or angiographic imaging arrangement are shown that can be used to support interventional procedures.

An example for such a procedure is trans-catheter arterial chemoembolization (TACE). To treat a liver tumor for instance, a catheter OB is introduced into the patient and advanced in general to a target vessel (such as the proper hepatic artery) that has been found to be a main feeder of the tumor. A volume or mass of embolization agent (hereinafter referred to as a "blob of glue", "embolus" or simply the "blob") is discharged through the catheter OB tip to occlude the vessel and to locally administer a chemotherapeutic drug that is included in the embolization agent as an admixture. The region of interest, ROI, where the deposition is to occur is, for example a portion of the above mentioned hepatic artery or a shunt of a vessel that needs to be occluded because patient needs to undergo AVM (Arteriovenous Malformations), arteriovenous fistula (AVF), or Hemangioma treatment. Examples of liquid embolization materials are ONYX® (ethylene vinyl alcohol copolymer, a glue-like substance), alcohol, or n-butyl cyanoacrylate (NBCA). Embolus administration commences at instant $t_0$ by releasing a volume of embolization agent via an open tip of said catheter near the ROI. Embolus then circulates in the bloodstream until it lodges in at a target position (usually a shunt linking the arterial to the venous systems), thereby occluding the blood vessel. During the deposition of the embolization an embolus builds up gradually and, during at least parts of said deposition, a series of sequential fluoroscopic images F are acquired by an x-ray imager 100. Another example for an embolization procedure is the treatment of tumors.

During the intervention, patient SP is deposed on a bed B between an x-ray imager 100's x-ray tube XT and detector D. X-ray tube XT and detector D are attached to rigid frame C rotatably mounted on a bearing B. The fluoroscopic image operation is controlled from a computer console CC. The interventional radiologist can control via said console CC image acquisition and can "shoot" a run of individual fluoroscopic frames ("fluoros") F by actuating a joy stick or a pedal. According to one embodiment, imager 100 is of the C-arm type but other systems are also envisaged.

During image acquisition X-ray radiation emanates from x-ray tube XT, passes through the ROI, experiences attenuation by interaction with matter therein, and the so attenuated beam p then strikes detector D's surface at one of plurality of detector cells making up detector D. Each cell that is struck by a beam responds by issuing a corresponding electrical signal. The collection of said signals is then translated into a respective digital value representative of said attenuation. The density of the material making up the ROI determines the level of attenuation with high density material causing higher attenuation than less denser materials. The so registered digital values for each x-rayp are then consolidated into an array of digital values forming a fluoro frame for a given acquisition time and projection direction. In other words each fluoro is a digital image of a projection view along a projection direction and said direction is determined by the rotation of the C-arm at the given acquisition time or instant. The series of fluoros F are then digitally processed by data acquisition unit DAS and are then forwarded to an image processer IPS whose purpose and operation will be explained in more detail below. In one embodiment detector D is a component of an image intensifier that directly projects the imagery on a screen M for real-time observation.

The stream of fluoroscopic frames F comprises in particular frames acquired whilst there is some embolization agent present at the ROI.

As will be explained in more details below, the frames are processed in a subtraction scheme to gather information about the embolization. For this purpose, the system further comprises an image processor IPS configured to act on the fluoroscopic image stream as furnished by the X-ray imager. Inset FIG. 1A shows details of the image processing system IPS as proposed herein.

The imaging system IPS includes an input port IN or receiving the fluoroscopic frames. The image processing system IPS further includes an image combiner MIF, a ROI focus motion compensator MCI that operates in co-operation with a landmark identifier LI, and subtractor DIFF to process the frames. The processed frames are then output as output imagery at port OUT. The output imagery may then be passed on to a visualizer to effect visualization of a graphics display GD on a display unit such as a monitor or screen MT. According to one embodiment there is a contrast measuring unit CMU and a substance deposition monitor FDM.

The IPS system as proposed herein helps furnish information on the embolization procedure. In one embodiment, deposition of the embolization agent at the region of interest ROI is visualized. Instead of or in addition to said visualization, in one embodiment the contrast measuring unit CMU is configured to compute based on the received fluoroscopic imagery the quantity e.g. volume of embolization agent deposited within a user definable period. This can then be used to compare the said volume with the actual volume administered at the ROI to so establish whether backflow events or other undesirable effects where some of the embolization agent is mistakenly deposited outside the ROI. The deposition monitor FDM may alert the user to this fact by issuing a suitable visual and/or acoustic alert signal.

Operation of the image processing system is broadly as follows. In real time mode, the received fluoroscopic frames are buffered in a suitable memory. All or a selection of the received frames are then registered onto each other to so compensate for any motion of the region of interest that may have occurred in the period between the respective frame F acquisition times. In one embodiment, the ROI is the location where deposition of the embolization agent occurs and is intended to occur. The motion compensation is thereby focused solely on the motion of the ROI. Other motions are not taken into consideration. The compensation is achieved by tracking by way of the landmark identifier LI a suitable landmark across the sequence of images. The landmark may be the actual footprint of the deposited blob of embolization agent and may also relate to a footprint of other anatomical or non-native landmarks for instance. According to one embodiment the landmark used is the footprint of the catheter tip for instance through which the embolization is discharged. The region of interest itself is then represented in the imagery as a user definable neighborhood for example a circle, square or other suitable section around the landmark. It is then this image portion representative of the region of interest around which the motion compensation is focused.

Once the sequence of fluoroscopic images or frames has been motion compensated or registered, the image combiner MIF operates to form, for given pair of instants, two images, a first image ("minuend") and a second image ("subtrahend"). In a simple embodiment the minuend or subtrahend may be a single, designated frame such as a current frame or maybe a frame from as per a specific user selected past instant. In one embodiment, at least one of the minuend or the subtrahend images are combined from all previous or a subset of fluoroscopic images into a sliding mask image as per:

$$M(t,n)=F(t-n)+F(t-n+1)+F(t-n+2)+ \ldots F(t) \tag{1}$$

The individual frames and/or the number of the frames so combined is automatically selected or is user selectable. In eq (1), t denotes the time index and n is an arbitrary constant used for the mask integration. In other words, n designates the number of images to be integrated. In other words, the sliding mask (1) is a combination of all or a sub-selection of n previous frames up to and including instant t. This instant t may be referred to herein as the time index of sliding mask or of the minuend or subtrahend frame/image.

According to one embodiment the combined sliding mask image (minuend and/or subtrahend) is formed from all (or a sub-selection of) previous n consecutive frames including the current frame at time t. According to one embodiment the masks may also be formed from every k-th (k>2) frame or from a collection of irregularly or randomly time-spaced frames rather than from a set of consecutive frames (that is, the frame are immediate temporal neighbors, there is no other frame between any two).

However, the minuend or subtrahend image may not necessarily be formed with respect to a current frame t. In particular in a replay or off-line mode (a non-real time mod) the user is free to specify any instant t and the image combiner then combines as per equation 1 the subtrahend and/or the minuend image into a corresponding sliding mask.

The minuend and subtrahend image are then forwarded to the subtractor DIFF module DIF to form a difference image for any two pairs of minuend and subtrahend images, for instance as per:

$$DI(t,t_i)=F(t)-M(t_i,n) \qquad (2)$$

$$DI(\tau)=M(t=t2,n)-M(t=t1,n), \text{ with } \tau=t2-t1 \qquad (3)$$

In the embodiment as per eq (2), the minuend is single (for instance the current) frame at time t (with sliding mask being built from frames at $t_i<t$) whereas in (3) the difference DI image is formed from minuend M(t=t2,n) and subtrahend M(t=t2,n) each combined from a plurality of frames as per eq (1), each sliding mask having a different index t1, t2.

The difference images are hence a function of the respective pair of time indices [(t1,t2) or $(t,t_i)$] of the minuend and subtrahend image. It will be appreciated that because of the ROI focused motion compensation performed prior to the forming of the minuend and subtrahend images the attenuation values recorded in the difference image are now solely attributable to the embolization agent deposited within those two time instances (that is the indices of the difference image). This is so, because of the correct alignment any other contribution from any intervening background, etc. has been cancelled out. Also, subtraction artifacts that may have occurred because of the motion of the ROI during acquisition are accounted by the image compensation.

The time indices t1,t2,ti etc. for the respective difference images DI are received at at time specification input interface T-IN. This may include text-based input means or preferably graphical user input means or touchscreen input means or any other user input functionality.

The difference image or a plurality of difference images DI formed for different pairs of instants $(t2,t1)_i$ are then forwarded to the visualizer VIS to effect display on monitor MT.

Each difference image is representative of and shows (when displayed) the accumulation of embolization agent during the two instants t2,t1 as represented by the time indices t1, t2 of the respective difference image. If a plurality of difference frames is formed these can be displayed chronologically in a cine or motion picture mode on the screen MT as indicated chronologically by frames A through B and C in FIG. 2. Each frame corresponds to a different difference image $DI(\tau_A)$, $DI(\tau_B)$ and $DI(\tau_A)$ as per eq (3). The intervals may be consecutive, non-consecutive (there may be time gaps between some or any two intervals), or they may be even overlapping, depending on the user selection/definition of the intervals $\tau_{A,B,C}$.

The embolization procedure itself is rather long winded and procrastinated procedure that can last for hours. The proposed image processing allows visualizing the deposition or parts thereof in a condensed form in fast motion. For instance, in the example in FIG. 2 an embolization procedure that lasted for forty minutes can be displayed in less than ten seconds for instance, depending on the time resolution chosen. The time resolution of the embolization cine sequence as per FIG. 2 can be adjusted by the user choosing a) the number of frames n from which the respective mask are to be combined from and/or b) the length of the time interval T=t1−t2, t−ti as per equation 3 and 2, respectively. For each difference image displayed, the later one of its time index (e.g., t2) may be interpreted as the "arrival time" of the quantity of embolization agent represented by said difference image. To more clearly render graphically the evolution of the embolization agent deposition at or around ROI, the different contributions (as encoded per each difference image) may be visually coded in a different manner on the screen in the accumulated graphics display GD shown in FIG. 2. In other words, the respective difference images are, in chronological order, superimposed on each other, one after the other to form an accumulative display to represent and "mimic" the actual accumulation of the deposition of the embolization agent. Each difference image newly superimposed on the already displayed difference images corresponds to the newly deposited "layer" of embolization agent may be visually encoded differently, for instance, may be rendered in a different color, hue or shading. In this manner a "color map" is formed that indicates with each color the layer of newly accrued volume of embolization agent during the respective intervals t2−t1 associated with each difference image. This color, hue or otherwise visually encoded "layer-by-layer" representation of the embolization deposition allows the user to recall as desired (based on the stockpile of previously recorded frames) the "broad picture" for any time period. In other embodiments, it is only the respective, newly added or superimposed difference image that is briefly highlighted in a certain color (which may be the same for each newly added difference image) and display of said newly added difference image than defaults to the natural grey level intensity. The respective new layers of embolization are then shown in a color flash or flare-up on display before defaulting back to grey.

As an alternative to the accumulated display of the various difference images DI, a sequential display in chronological order of the difference images is also envisaged where the difference images are not superimposed but are displayed in sequence one by one and one instead of the other.

In another visualization mode, a "trace image" may be formed by choosing different time resolution n (as in eq (3)) for the first image and the second image and/or two different instances of time—one for the first image and one for the second image.

Figure 3:
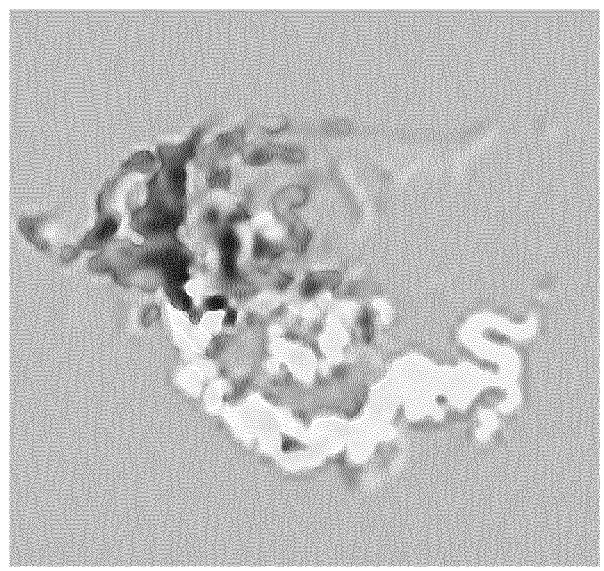
FIG. 3 shows a representation of a graphics display according to another embodiment produced by the arrangement of FIG. 1.

As an alternative and as shown as FIG. 3, the arrival times themselves are color coded in an overlay. The overlay as per FIG. 3 shows the relative arrival time for each deposition, for instance the darker the hue, the earlier the deposition occurred whereas the lighter the hue the more recent the deposition, with the latest showing up at any instant as the lightest of hues. Other visual encoding such as by hue, shading etc. are also envisaged in alternative embodiments.

Figure 2:
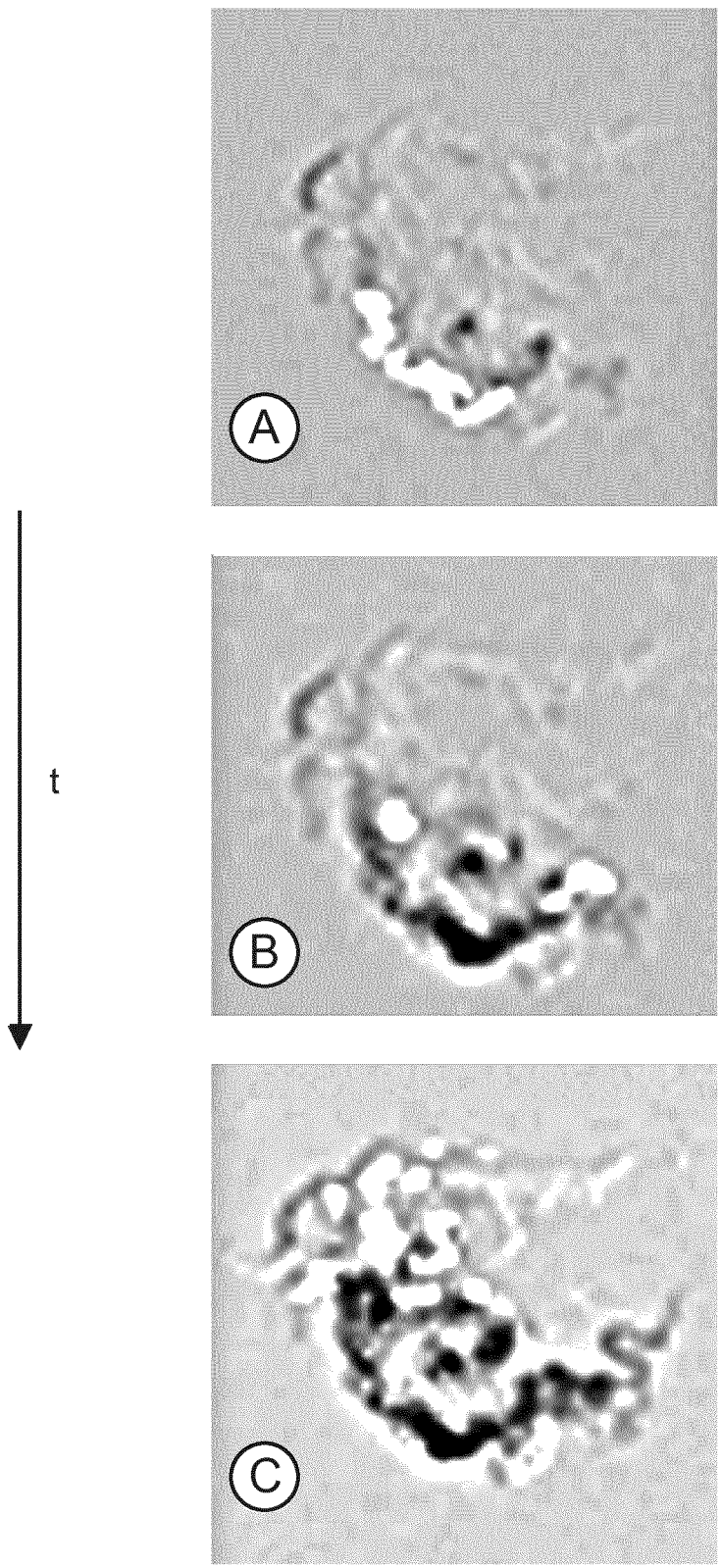
FIG. 2 shows a representation of a graphics display according to one embodiment produced by the arrangement of FIG. 1.

The respective visualizations as per FIGS. 2 and 3 could be shown next to a live image or as a guidance overlay of the current image upon user request.

As an alternative, given a current frame Ft, the user can define a time index in the past, say $t_i$, by a slider GUI widget or any other input means T-IN to so instruct image former MIF to form a combined mask as per eq (2). When visualizing this difference image as per equation 2, no deposition will be shown prior to time instance Only depositions after $t_i$ will be visible. This allows the user to visually examine the progress made during the procedure.

In all of the above display modes, the user selection of time instants t1,t2 or $t_i$ may be invited, as mentioned in the earlier paragraph, by means of one or more virtual sliders (e.g. two triangles having one of their respective vertices point toward each other, but any other symbology is also envisaged herein) that can be dragged by mouse-click or touchscreen action over a virtual timeline to so define the respective time intervals. In one embodiment, there is semi-automatic support for these interval selections: the user selects only a first interval and then the system goes automatically "back in time" to define a plurality (exactly how many is either a default number or is user adjustable) of contiguous time intervals having the same length as the first, user defined one. An event handler then passes on the plurality of time intervals $(t2,t1)_i$, and the respective selections of associated frames are then processed by combiner MIF and subtractor DIFF as explained above and the then respective difference images DI are then displayed in the desired display mode as discussed above at FIGS. 2,3.

Figure 4:
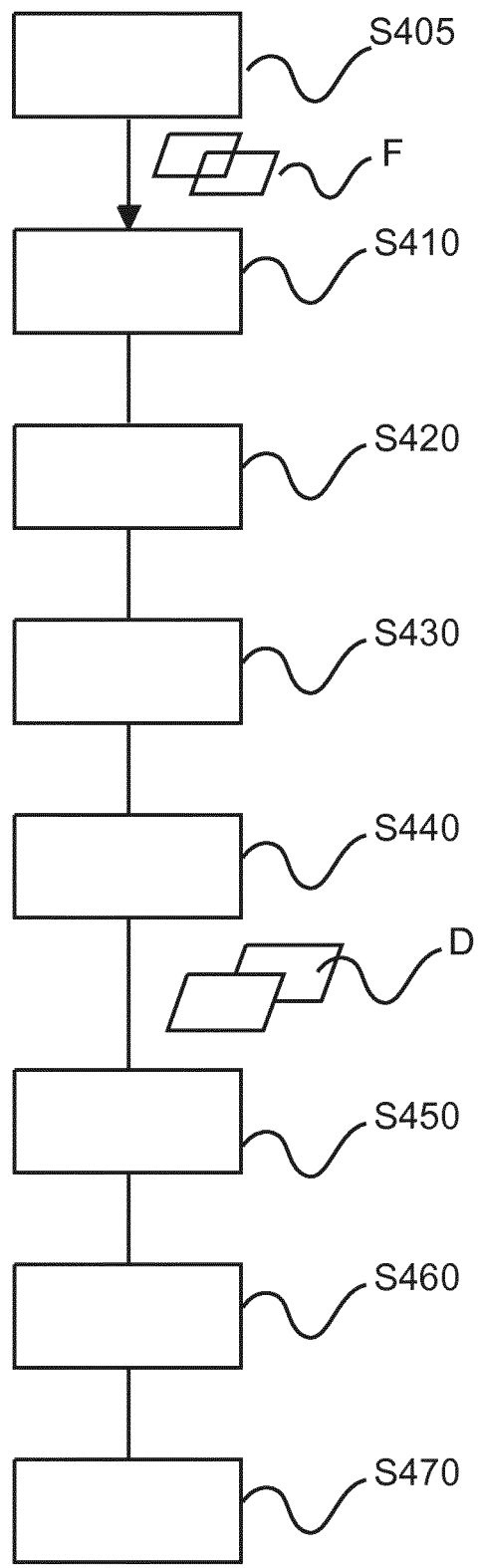
FIG. 4 shows a flow chart of an image processing method.

Turning now to flow charts in FIG. 4 the image processing method underlying operation of image processor IPS is now explained in more detail.

At step 405 a stream of (two or more) fluoroscopic images F is received. The image acquisition would normally start prior to the actual deposition of the embolization agent, would then cover the period of time during which the deposition occurs and would then end at the conclusion of the deposition. However, other scenarios are envisaged where not the whole of the deposition is imaged, but imaging is on different image runs with interruptions between any two of said runs. In one embodiment, image acquisition commences only after the deposition has commenced. However, each frame has a respective index indicating its acquisition time. In other words, whether or not the whole procedure has been imaged, or has been imaged in different image runs, the individual frames can be reconstructed into a chronological time sequence using the time indices of the individual frames.

At step S410 a selection for frames to be combined into the subtrahend or the minuend image are motion compensated in respect of the location where the deposition is to occur or has occurred. Using rigid or non-rigid motion tracking techniques or optical flow algorithms limited to the ROI footprint, the motion compensation is focused on an image portion representative of the ROI only. In other words, the motion of said image portion is followed in isolation from motions of other image objects in other motion layers. The motion compensation in one embodiment includes landmark identification or following a specific landmark across the sequence of images. The landmark may be the location of the actually embolized tissue but may also be taken to be that of a catheter tip or other medical tool resident during the deposition of the embolization agent. The motion of the ROI image portion may also be done in proxy, that is, a landmark is tracked across the frames whose motion is a prior-known to be in a deterministic relationship with the ROI image portion motion. The landmark motion can then be converted in the ROI motions by a suitable conversion. The information about the ROI image portion gathered during the tracking is then used to effect the registration of the frames (of the minuend and the subtrahend image, respectively) by mutual alignment to compensate for the motion of the ROI image portion as recorded in the frames. In other words, after the registration, the ROI image portion in the frames is at substantially the same position relative to a global fixed coordinate system. In this manner, motion imparted by cardiac or respiratory (or both) or any other patient SP motion can be eliminated.

At step S420 a first and second image (minuend and ubtrahend image) are then formed from respective frames so registered. The subtrahend image in particular may be taken to be a single frame for instance the current frame if the method is practiced in real time mode although off-line applications are also envisaged where the single frame subtrahend can be taken to be any desired frame from the recorded stream of frames. Either the minuend or the subtrahend image, or both are formed as a combination of at least two images as per eq (1) above. In other words, a selection of plurality of the frames, acquired at suitable acquisition times, up to latest time index t1 or t2 is collapsed into a combined image $M(t1,n)$ or $M(t2,n)$ to form the minuend and/or the subtrahend image. The combination may be by a pixel-wise addition, but other forms of frame combinations, such as temporal or spatial averaging or filtering of a suitable number of frames per subtrahend or minuend image, are also envisaged. The number and/or identity of frames to be used for forming the subtrahend and/or the minuend image is user adjustable.

At step S430 one or more difference images are formed by subtracting the respective first image from the respective second image. Each difference image is then representative of the accumulated deposition of embolization at the region of interest during the respective time instants ($T=t2-t1$ or $=t-t1$) of the two sliding masks from which the difference image has been formed (eq (3)) or during the period $\tau=t-t_i$ between the current frame and the index of the sliding mask used to form the difference image (eq(2)).

In one embodiment, different time resolutions can be chosen so as to determine the degree or level of fast motion in the later visualization of the difference images as a motion picture on screen MT. The time resolution is determined by the respective time intervals T between the indices (t1 and t2 or t and $t_i$) of the minuend or subtrahend images used for forming the respective difference image.

At step S440 the one or more difference images D are then output for further processing or storage etc.

At step S450 the output difference image(s) is/are displayed on a display device such as monitor or screen MT. The difference images are displayed superimposed on each other to form an accumulative or sequential motion picture or cine image representing the time evolution of the deposition. Each or some of the difference images may be displayed in different visual renderings such as color, hue or otherwise. According to one embodiment the visualization may include forming a trace image. All display modes as described above in FIGS. 2 and 3 are envisaged herein.

At step S460 the image information in the one or more difference images are converted into numerical form to indicate the volume or mass or concentration of embolization agent deposited between the respective time instants. This can be done because the contrast as represented in the difference images are solely attributable to the embolization agent. This is assured by the forming of the above ROI focused motion compensation and also by subtracting out the intervening background object contributions. Computation of the deposited quantity of embolization agent is based on the Beer-Lambert Law. It is further assumed herein that at least one of the following parameters is known: the beam quality of the actual fluoroscopic system used for the acquisition, and the x-ray absorption characteristic of the embolization agent. More particularly, it is assumed that the X-ray linear absorption coefficient as a function of the X-ray energy of the specific embolization agent is known. This can be computed once the chemical composition of the embolization agent is known. The absorption coefficient can also be measured. See for instance, Hubbell, J. H. and Seltzer, S. M. (2004), "Tables of X-Ray Mass Attenuation Coefficients and Mass Energy-Absorption Coefficients" (version 1.4 as per 8 Oct. 2014), available online at http://physics.nist.gov/xaamdi, National Institute of Standards and Technology, Gaithersburg, M.D. It has been observed that very good results can be achieved if the linear absorption co-efficient of the embolization agent is substantially different from the surrounding tissue.

The actual image pixel intensity in each difference image is proportional to the attenuation suffered by the ray of the X-ray beam impinging at a detector pixel associated with said image pixel. Because the initial energy of the ray is known, the recorded attenuation can be translated (via the linear absorption co-efficient) into a corresponding "in-embolus" path length, that is, a path length through the embolus which the respective x-ray has travelled before impinging on said pixel. This defines for each pixel a prism as a primitive volume element whose height corresponds to said in-embolus path length. The above procedure can be repeated for each pixel in the footprint of the embolization mask and the results (that is, the respective volume prisms for each pixel) can be integrated to arrive at a numerical estimate for the (average) embolus volume during the respective period T.

At step S470, the computed numerical volume is then compared with a theoretically expected volume deposition as computed from a known flow rate or injection rate and the time indices of the considered difference image. The computed image volume is expected to essentially equal the total of injected embolization agent between the two time instants. However, if there is a deviation and if this deviation violates a pre-defined threshold an alert signal is issued. This is because there is a danger that some of the embolization agent has been ill deposited at locations outside the ROI which may be undesirable. In other embodiments using the time indices for the respective difference frame a flow rate can be established by forming the ration of the computed volume versus the time period T as per the two time indices t1,t2 for any difference image.

In step S480, the numerical values as per steps S460 or S470 are output. In one embodiment, it is the flow rate themselves that may be visually indicated by suitable visual rendering of the difference images. In addition, or as an alternative, in step S480, a visual indication of the total volume of embolization agent deposited may be output either numerically or as a color overlay on the respective difference image(s). In one embodiment, a visual or auditory signal may be issued to indicate that a certain pre-defined threshold has been reached.

In other words and/or as an extension of what has been described, the following visual or audible cues (and any combination thereof) are envisaged herein for output at step S480 during the embolization injection to assist the user during the procedures:

visual/audio signal to indicate backflow of the embolization agent visual/audio signal to indicate significant deposition and or flow outside of the target area visual indication of the measured injection rate, either in number or with colors denoting different injection rates visual indication of the total amount of embolization agent deposited, either numerically, or as a color or otherwise visually encoded overlay visual/audio signal to indicate a certain predefined threshold has been reached.

In sum, and as will be understood from the above, the proposed system IPS harnesses the fact that, contrary to usual "fleeting" angiographic contrast agent, the slow dynamics and resident property of materials of higher viscosity such as embolic materials (it remains in the tissue), makes the computing of the extent of the embolized region extent directly computable from the above data and from the integral of the total embolic absorption over the ROI (e.g., the tumor inflicted area). If the injection rate is known, temporal differences can also be involved to indirectly monitor the flow outside the ROI. More specifically, this out-of ROI flow is, the difference between the amount of injected embolization agent per unit of time, and the observed deposition in the ROI during the same interval). The injection rate itself can be deduced from interfacing with the control electronics or interface of the injector mechanism, or from some dedicated measurement device (such as a flow meter or ultrasound/Doppler device, etc.), or may be deduced purely image based from flow-measurement algorithms. These purely image based algorithms of flow determination may be based on 3D models of the catheter tip or of some main vessels or vessels of interest. Iterative filtering of flow/deposition may be used based on the know injection characteristics. For instance, one may assume essentially all of the embolization agent is deposited in the target ROI. One then uses the mass conservation law to estimate the flow. Integrating the estimated flow will then result in an estimate for the total deposition, and this procedure may then be repeated in a number of iterations.

Although operation of image processor system IPS has been explained with reference to projection X-ray imaging, the method is of equal application to 3D imagery, such as obtained from computed tomography (CT) imaging or others.

The image processing module IPS may be arranged as a software module or routine with suitable interfaces to read in the fluoro stream F and may be run on a general purpose computing unit or a dedicated computing unit. For instance, processor IPS may be executed on a workstation or console CC of the imaging system 100. The image processing module IPS with some or all of its components of may be resident on the executive agency (such as a general purpose computer, workstation or console) or may be accessed remotely/centrally by the executive agency via a suitable communication network in a distributed architecture.

Alternatively, the components of the image processing module IPS may be arranged as dedicated FPGAs (field-programmable gate array) or similar standalone chips. The components may be programmed in a suitable scientific computing platform such as Matlab® or Simulink® and then translated into C++ or C routines maintained in a library and linked when called on by the executive agency such as the general purpose computer, workstation or console.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing system, comprising:
   an input port configured to receive a plurality of images acquired of a region of interest, ROI, in a specimen at different instants before, during or after an administered volume or mass deposition of a substance at or around said ROI, wherein the substance comprises an embolization agent;
   an image combiner configured to produce, for a given pair of time indices that comprise a first instant, $t_1$, and a second instant, $t_2$, at least (i) a first image from a combination of any of at least a subset of the plurality of said images acquired up to and including the first instant, and (ii) a second image from a combination of any of at least a subset of the plurality of said images acquired up to and including the second instant, wherein at least one of the first image and the second image comprises an integrated combination of n images, wherein n designates more than one of the plurality of images;
   a subtractor configured to subtract the first image from the second image to obtain a difference image as a function of a respective pair of time indices of the first and second image that represents a given volume or mass accumulation of said substance deposited at or around said ROI between the first instant and the second instant;
   a contrast measuring unit that measures a quantity of the given volume or mass of accumulated substance deposited at or around said ROI between the first instant and the second instant based on (i) the difference image and (ii) a known X-ray absorption characteristic of the substance, and
   an output port configured to output said difference image, and/or a numerical indication of the measured quantity, of the given volume or mass of accumulated substance deposited at or around said ROI between the first instant and the second instant.

2. An image processing system as per claim 1, wherein the first image or second image is a spatially or temporally filtered image.

3. An image processing system as per claim 1, wherein the system operates to output a plurality of difference images for different first and/or second instants, the system further comprising a visualizer configured to effect sequential display of said plurality of difference images on a display unit.

4. An image processing system as per claim 3, wherein at least two of said difference images are displayed in different visual renderings.

5. An image processing system as per claim 1, including a ROI focused motion compensator that operates to register, before the image subtraction, the plurality of images to motion compensate for motion of the ROI between acquisition of individual images.

6. An image processing system as per claim 5, wherein the motion compensator cooperates with a landmark identifier configured to identify across the images a landmark that corresponds to the ROI or to a device operative to deposit said substance.

7. An image processing system as per claim 6, wherein the first and/or second instant is/are user adjustable.

8. An image processing system as per claim 7, wherein the number of the images combined by the image combiner into the first image or into the second image is user adjustable to thereby adjust a time resolution at which the accumulation of the substance is displayed.

9. An image processing system as per claim 1, further comprising a substance deposition monitor configured to compare i) the volume of said substance administered to the specimen between the two instants with ii) the measured quantity of said volume of substance deposited as per the difference image, the deposition monitor configured to issue an alert signal if a discrepancy between the two volumes exceeds a threshold.

10. An image processing method, comprising the steps of:
    receiving, via an input port, a plurality of images acquired of a region of interest, ROI, in a specimen at different instants before, during or after an administered volume or mass deposition of a substance at or around said ROI, wherein the substance comprises an embolization agent;

producing, via an image combiner, for a user defined time interval between given pair of time indices that comprise a first instant, $t_1$, and a second instant, $t_2$, at least (i) a first image from a combination of any of at least a subset of the plurality of said images acquired up to and including the first instant, and (ii) a second image from a combination of any of at least a subset of the plurality of said images acquired up to and including the second instant, wherein at least one of the first image and the second image comprises an integrated combination of n images, wherein n designates more than one of the plurality of images;

subtracting, via a subtractor, the first image from the second image to obtain a difference image as a function of a respective pair of time indices of the first and second image that represents a given volume or mass accumulation of said substance deposited at or around said ROI between the first and second instant;

measuring, via a contrast measuring unit, a quantity of the given volume or mass of accumulated substance deposited at or around said ROI between the first instant and the second instant based on (i) the difference image and (ii) a known X-ray absorption characteristic of the substance; and outputting, via an output port, said difference image, and/or a numerical indication of the measured quantity, of the given volume or mass of accumulated substance deposited at or around said ROI between the first instant and the second instant.

11. A non-transitory computer program component for controlling a system, which, when being executed by a processing unit, is adapted to perform the method steps of claim 10.

12. A non-transitory computer readable medium having stored thereon the program element of claim 11.

13. An image processing system as per claim 1, wherein the second image is a single image acquired at the second instant.

* * * * *